(12) United States Patent
Bankiewicz (10) Patent No.: US 11,583,311 B2
(45) Date of Patent: *Feb. 21, 2023

(54) ADJUSTABLE STEPPED CANNULA (71) Applicant: THE REGENTS OF THE UNIVERSITY OF CALIFORNIA, Oakland, CA (US)

(72) Inventor: Krystof Bankiewicz, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/921,604

(22) Filed: Jul. 6, 2020

(65) Prior Publication Data
US 2020/0337721 A1 Oct. 29, 2020

Related U.S. Application Data (63) Continuation of application No. 15/525,548, filed as application No. PCT/US2015/060421 on Nov. 12, 2015, now Pat. No. 10,758,264.

(60) Provisional application No. 62/079,393, filed on Nov. 13, 2014.

(51) Int. Cl.
A61M 5/158 (2006.01)
A61B 17/34 (2006.01)
A61M 5/46 (2006.01)
A61M 5/32 (2006.01)
A61B 6/12 (2006.01)
A61B 17/00 (2006.01)

(52) U.S. Cl.
CPC ............ *A61B 17/3421* (2013.01); *A61B 6/12* (2013.01); *A61B 17/3478* (2013.01); *A61M 5/158* (2013.01); *A61M 5/3286* (2013.01); *A61M 5/46* (2013.01); *A61B 17/3417* (2013.01); *A61B 2017/00991* (2013.01); *A61B 2017/3433* (2013.01); *A61B 2017/3443* (2013.01); *A61B 2017/3454* (2013.01); *A61M 2206/20* (2013.01); *A61M 2210/0693* (2013.01)

(58) Field of Classification Search
CPC ............ A61B 17/3421; A61B 17/3417; A61B 2017/00991; A61B 2017/3443; A61M 5/46
See application file for complete search history.

(56) References Cited

U.S. PATENT DOCUMENTS

6,186,986 B1 2/2001 Berg et al.
8,083,720 B2 12/2011 Solar et al.
9,089,667 B2 * 7/2015 Bankiewicz ...... A61M 25/0662
(Continued)

Primary Examiner — Laura A Bouchelle
(74) Attorney, Agent, or Firm — Edward J. Baba; Bozicevic, Field & Francis LLP (57) ABSTRACT The use of stepped cannulas, wherein a step structure creates a backstop to reduce backflow along the cannula body, is known for convection enhanced delivery of agents to the brain and other structures within an animal. Described herein are novel and improved stepped cannula designs wherein the length of the cannula segment between the step and the dispensing outlet is variable and can be controllably adjusted inside the patient during delivery. This advantageously allows the operator to place the cannula step at the optimal position and deliver agents at one or more positions within the target structure.

15 Claims, 5 Drawing Sheets (56) References Cited

U.S. PATENT DOCUMENTS

| | | | |
|---|---|---|---|
| 9,919,129 B2* | 3/2018 | Singh | B29C 33/0061 |
| 10,758,264 B2* | 9/2020 | Bankiewicz | A61B 17/3478 |
| 2003/0109852 A1 | 6/2003 | Peterson et al. | |
| 2004/0082905 A1* | 4/2004 | Solar | A61M 25/0662 |
| | | | 604/264 |
| 2005/0234393 A1 | 10/2005 | Wood | |
| 2009/0198218 A1* | 8/2009 | Gill | A61M 25/02 |
| | | | 604/524 |
| 2011/0046552 A1 | 2/2011 | Bankiewicz et al. | |
| 2012/0209110 A1 | 8/2012 | Bankiewicz et al. | |
| 2013/0079748 A1 | 3/2013 | Bankiewicz et al. | |
| 2013/0253474 A1 | 9/2013 | Farhangnia et al. | |
| 2013/0261565 A1 | 10/2013 | Wong et al. | |

* cited by examiner

ADJUSTABLE STEPPED CANNULA

CROSS-REFERENCE TO RELATED APPLICATIONS

This application is a continuation of and claims priority to U.S. patent application Ser. No. 15/525,548, entitled "Adjustable Stepped Cannula," filed on May 9, 2017, which is a 371 national stage application of International Patent Application Number PCT/US2015/060421, entitled "Adjustable Stepped Cannula," filed on Nov. 12, 2015, which claims priority to U.S. Provisional Application Ser. No. 62/079,393 entitled "Adjustable Stepped Cannula," filed Nov. 13, 2014, each of which is incorporated by reference herein in its entirety.

STATEMENT REGARDING FEDERALLY SPONSORED RESEARCH OR DEVELOPMENT

This invention was made with government support under grant number R01 NS073940 awarded by the National Institutes of Health. The government has certain rights in the invention.

REFERENCE TO SEQUENCE LISTING, A TABLE, OR A COMPUTER PROGRAM LISTING COMPACT DISK APPENDIX

Not Applicable.

BACKGROUND AND SUMMARY OF THE INVENTION

The direct delivery of agents to specific target regions of the brain is emerging as an essential tool in the treatment of cancers, neurodegenerative conditions, and other pathologies of the central nervous system. Convention-enhanced delivery (CED) is a preferred method of delivering agents to selected regions of the central nervous system, especially the brain. In CED, a cannula is inserted into the target organ, and aided by direct radiographic visualization, the tip of the cannula is placed in the target structure, such as a specific anatomical feature or tumor. Therapeutic agents such as viral vectors, growth factors, or chemotherapeutic agents are then dispensed from the tip of the cannula at a sufficient rate (for example, 0.2-100 µL/min) to induce a pressurized bulk flow and efficient distribution of the agent by convective flow.

Figure 1:
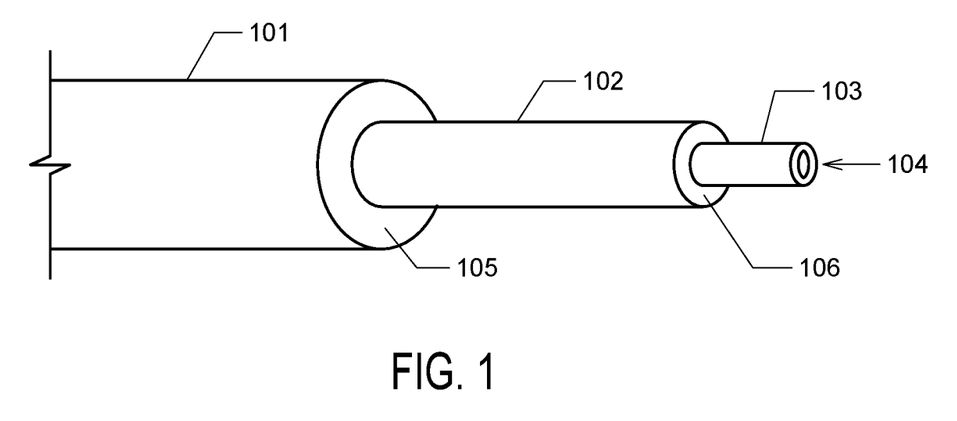
FIG. 1 depicts an exemplary stepped cannula. The cannula comprises a body (101), an intermediate section (102) having a reduced diameter compared to the body, which such reduction in diameter at the junction of the body and intermediate section forms a major step (105). A tip portion (103), having a distal opening (104) from which solution is eluted, is of a smaller diameter than the intermediate section, forming a minor step (106) at the junction of the intermediate section and tip portion.

A significant problem in CED is the tendency of the delivered solution to backflow along the cannula track. To address this problem, "stepped" cannulas were developed. The step is an abrupt reduction in diameter between the proximal region of the cannula body and the distal end (from which the agent solution is dispensed). Typically, the step is a face or surface perpendicular to the long axis of the cannula which surrounds the diameter or perimeter of the cannula. Cannula designs having a major step and a minor step, for example, as depicted in FIG. 1, may be used. Advantageously, it was discovered that the step creates a backstop which blocks backflow of infused solution and promotes the even distribution of the agent throughout the target area. Exemplary stepped cannulas are described in U.S. Patent Application Publication No. 2013/0079748, entitled "Stepped Cannula," by Bankiewicz et al.

In CED, localized delivery of the agent, confined within the target region, is essential. Often, the delivered agent is selectively beneficial, being therapeutic within the target region but having a detrimental effect on other regions of the brain. Off-target delivery of agents is wasteful at best, and at worst can result in substantial, negative side effects. For example, a chemotherapeutic agent delivered to a tumor is desirable, but it is undesirable that the chemotherapeutic agent be distributed beyond the region of the tumor.

In practice, it is difficult to select an appropriately sized cannula which will achieve the ideal spacing between the dispensing tip and the step. Once the cannula is inserted into the target area, the operator may observe that the distance between the dispensing tip and major step is too long, as in FIG. 2A. In such case, in order to keep the dispensing tip centered in the target structure, the major step is located outside of the target structure, and the backflow of dispensed solution to the step results in solution being delivered outside of the target structure. Alternatively, the distance between the dispensing tip and the major step may be too short, as in FIG. 2B. When the distance between the step and dispensing tip is too long or too short, the major step cannot be placed at the boundary or opening of the target region while simultaneously placing the dispensing tip within the middle of the target region for optimal delivery. Accordingly, there is a need in the art for CED systems which allow for precise delivery of agents to a target region.

The cannula designs and associated methods disclosed herein provide the art with new cannulas and methods of use which allow for accurate delivery of therapeutic solutions to target regions in the brain or other structures. The novel cannula designs of the invention are adjustable, allowing for placement of the step in the optimal position to minimize off-target delivery.

BRIEF DESCRIPTION OF THE DRAWINGS

FIG. 1.

FIGS. 2A, 2B, and 2C.

FIG. 3.

FIGS. 4A, 4B, and 4C. FIGS. 4A, 4B, and 4C depict the delivery of solution to a target structure using an adjustable stepped cannula of the invention, with the tip in three different positions. FIG. 4A depicts the adjustable cannula deployed with the adjustable tip deployed in an extended configuration. The cannula is (011) administering solution (408) to a target structure (401) with the body tube (403) positioned such that the major step (404) is optimally placed at the boundary or opening (402) of the target structure and the adjustment tube (405) extended such that the distal opening (407) of the dispensing tip (406) is in a first position.

FIG. 5.

DETAILED DESCRIPTION OF THE INVENTION

Figure 2A:
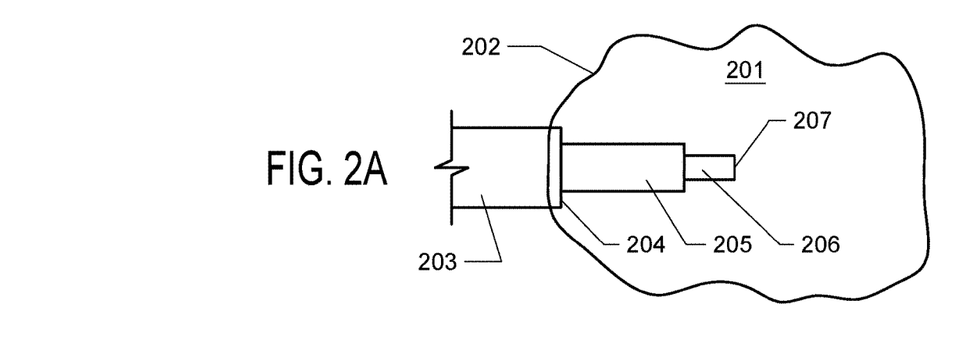
FIG. 2A depicts the optimal placement of a stepped cannula within a target structure (201), wherein the major step (204) is located at the boundary or opening of the structure (202) and the distal opening (207) of the dispensing tip (206) is located in the center of the structure.
Figure 2B:
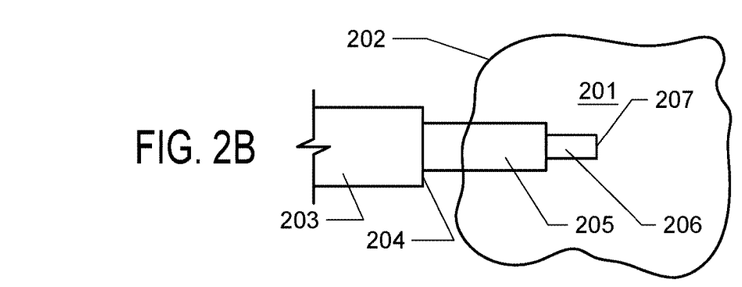
FIG. 2B depicts a prior art, non-adjustable cannula in a target structure (201), wherein the distance between the dispensing tip (206) and the major step (204) is too long and the major step (204) is located outside the boundary or opening (202) of the target structure.
Figure 2C:
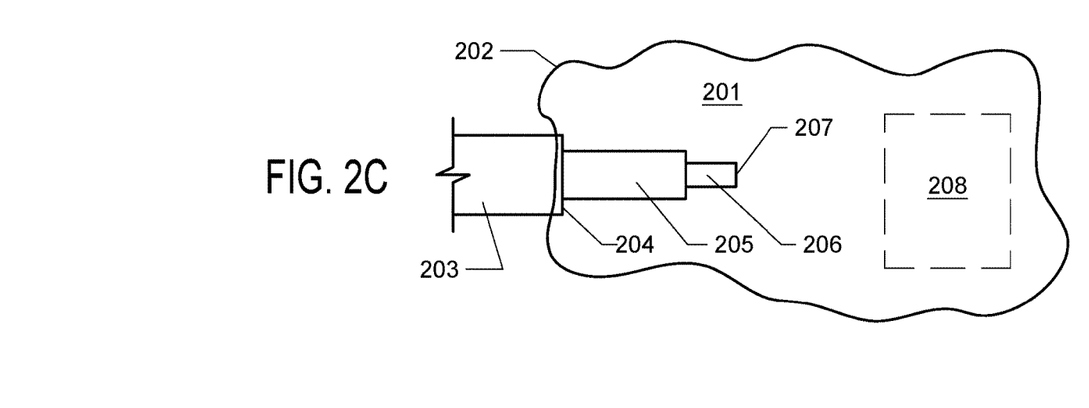
FIG. 2C depicts a prior art, non-adjustable cannula in a target structure (201), wherein the distance between the dispensing tip (206) and the major step (204) is too short. When the cannula is properly placed with the major step (204) located at the boundary or opening (202) of the target structure, solution flowing from the distal opening (207) of the dispensing tip (206) will not effectively cover the target structure, leaving a region of the target structure (208) untreated or undertreated.

When utilizing a stepped cannula for CED, ideally, the infusion tip is placed in the center of the target structure and the major step is located slightly within the boundary or opening of the target structure, as depicted in FIG. 2A. The major step, within the boundary or opening of the structure, creates a backstop and inhibits backflow along the cannula out of the target region. The minor step or steps, if present, aid in the dispersion of the delivered solution by disrupting backflow. Optimal cannula placement is described in United States Patent Application Publication Number US2012/0209110, entitled "Optimized Placement of Cannula for Delivery of Therapeutics to the Brain," by Bankiewicz et al.

Provided herein is a novel adjustable stepped cannula design. Advantageously, the adjustable stepped cannula allows the distance between the distal end of the dispensing tip and the major step to be adjusted inside the patient. The scope of the invention encompasses any cannula wherein the distance between the distal end of the dispensing tip (from which solution is flowed) and a step can be lengthened or shortened by an operator while the cannula is deployed in vivo. Such a cannula can be configured in various ways. Typically, the adjustable stepped cannula of the invention is telescoping, such that the dispensing tip can be extended from or retracted into a body. For example, in one embodiment, the cannula comprises a design as depicted in FIG. 1, wherein the length of section 102 can be adjusted.

The adjustability of the novel cannulas of the invention allows the operator to customize the instrument to the actual geometry of the target region, as visualized by radiographic imaging (e.g. MRI) during the infusion procedure. Additionally, the adjustable stepped cannula designs of the invention allow the operator to place both the major step and the tip in optimal position, with a major step located at the boundary (or opening, in the case of a pocket-like structure) of the target structure to prevent backflow out of the structure, and the tip deployed to a position such that delivered solution will be optimally placed. Importantly, using the adjustable stepped cannulas of the invention, the cannula can be placed such that the major step remains in a single location while the tip is lengthened or shortened to multiple positions from which solution is dispensed. This allows the operator to deliver solution along an elongated profile, for example conforming to an oblong target structure in the brain. Another advantage of the adjustable stepped cannulas of the invention is that the major step can be held in place at the opening of a target structure during infusion such that the opening is wholly or partially occluded. This allows the infused solution to create a slight pressurization within the target structure, which, in some cases, acts to seal the structure from leakage, for example perivascular leakage. This sealing effect advantageously prevents the leakage of infused agent from the structure.

The adjustable stepped cannula of the invention comprises various elements. At the most basic level, the cannula comprises a body, having a proximal to distal orientation, with the proximal end being located outside the patient, towards the operator, and the distal end, from which material is flowed into the patient, being inserted into the target structure. A telescoping element that will be referred to as an "adjustable tip" protrudes from the body. The stepped cannula of the invention further comprises a major step, i.e. an abrupt reduction in diameter or width between the body and the adjustable tip, for example, a step being a surface substantially perpendicular to the long axis of the body. The reduction in width or diameter between the dispensing tip and the body may be, for example a 30-80% reduction in width or diameter.

The cannula is configured such that the adjustable tip is telescoping, wherein the distance between the major step and the distal end of the adjustable tip, from which solution is flowed into the patient, can be lengthened or shortened extending or retracting the adjustable tip from or into the body. This distance will be referred to as "tip length." Tip length can be adjusted by an operator, by action of an adjustment mechanism, as described below.

The adjustable tip may comprise a single tube, or may comprise multiple elements, e.g. an assembly, for example an assembly of conjoined concentric tubes. In one embodiment, the adjustable tip comprises an intermediate body and an inner body which projects from the distal end of the intermediate body. The inner body, if present, will be referred to as the dispensing tip. The dispensing tip is the most distal element of the cannula and has an opening from which delivery solution flows. Typically, there is a reduction in diameter between the intermediate body and the dispensing tip forming a minor step, for example as in FIG. 1 where minor step 106 is disposed between the distal opening of the dispensing tip 104 and the major step 105. In some embodiments, multiple reductions in diameter are present on the intermediate body, creating additional minor steps.

The cannula body will be of sufficient length that its distal end can be inserted into the target structure of a selected animal while the proximal end of the cannula protrudes from the animal, where it can be controlled and positioned by the operator. The cannula comprises an internal lumen in the telescoping portion, which on the proximal end is connected to a supply of delivery solution. The proximal end of the telescoping element will typically comprise a fitting, for example a Luer adapter, which allows the connection of the cannula to flexible tubing, such tubing being in connection with the delivery solution supply. The supply may comprise a vessel for holding the solution liquid and pump, syringe or other mechanism for causing solution to flow into the cannula at a controllable rate. The delivery solution comprises a carrier liquid containing an agent, (e.g. a therapeutic agent). When the delivery supply is engaged, delivery solution flows through the cannula and exits the distal end of the lumen into the target structure of the patient.

The proximal end of the cannula of the invention comprises an adjustment mechanism which enables an operator to shorten or lengthen the tip length in a controlled manner. The invention is not limited to any specific adjustment mechanism, and encompasses any part(s), device(s), or combination of parts or devices which allow the controlled adjustment of tip length. In one embodiment, the adjustment mechanism comprises a body which protrudes from the proximal end of the body tube and also comprises a handle or grip. This handle or grip of the adjustment tube can be gripped manually by the operator and pulled or pushed to adjust the tip length. In an alternative embodiment, a mechanical force actuator mechanism, either manually powered or powered by a motor, is used to adjust the length of the tip. For example, the actuator may comprise a gear mechanism which can engage teeth, indentations or projections on a telescoping element of the cannula, wherein turning of the gear can be used to extend or retract the adjustable tip. The gear may be under manual control (for example, by use of thumbwheel), or may be moved by a motorized actuator, for example, a computer controlled motorized actuator. In an alternative embodiment, the adjustment mechanism comprises sections of complementary threading on the outer surface of the adjustment tube and inner surface of the body tube. In this embodiment, the adjustment tube can be rotated within the body tube by manual action or a motorized actuator, such that the adjustment tube moves proximally or distally along the long axis of the body tube as it is rotated.

In some embodiments, an ancillary function of the adjustment mechanism is to secure the telescoping in place, once the desired tip length has been set. Alternatively, the cannula may comprise a separate locking mechanism that is engaged when the position of the adjustable tip is as desired. For example, cotter pin and holes, crimping locks, clamping locks, screw locks, set screws, and other such devices known in the art and used to arrest the movement of a telescoping element may be used.

An optional feature for the cannula of the invention is an indicatorechanism which aids the user in precisely adjusting the length of adjustable tip. For example, the indicator mechanism may comprise a slot or opening in the body which allows graduated markings, corresponding to tip length, on the outer surface of the telescoping element to be observed. In another embodiment, the indicator mechanism may comprise a portion of the telescoping element which protrudes from the proximal end of the body and which comprises markings corresponding to tip length. In another embodiment, the indicator mechanism is an analog or digital readout from an actuator (e.g. motorized gear assembly) which is used to extend and retract the telescoping element.

In another embodiment, the cannula of the invention may further comprise one or more radio-opaque markings, which are visible to the operator via the selected radiological imaging modality used to place the cannula, in order to aid the operator in positioning the cannula. The markings may be made by the adornment of the cannula structures with radio-opaque materials, such as gold, titanium, etc. One or more radio-opaque markings may be present on or near the major step. One or more radio-opaque markings may also be present at or near the distal opening of the adjustable tip. One or more scale or reference markings, for example a bar of a known length, or a series of lines, dots or gradations at fixed intervals, may be used and can act as a ruler that allows the operator to measure the required degree of adjustment of tip position for optimal tip placement. The operator may then effect the desired adjustment via the adjustment mechanism, optionally with the aid of the indicator mechanism.

Figure 3:
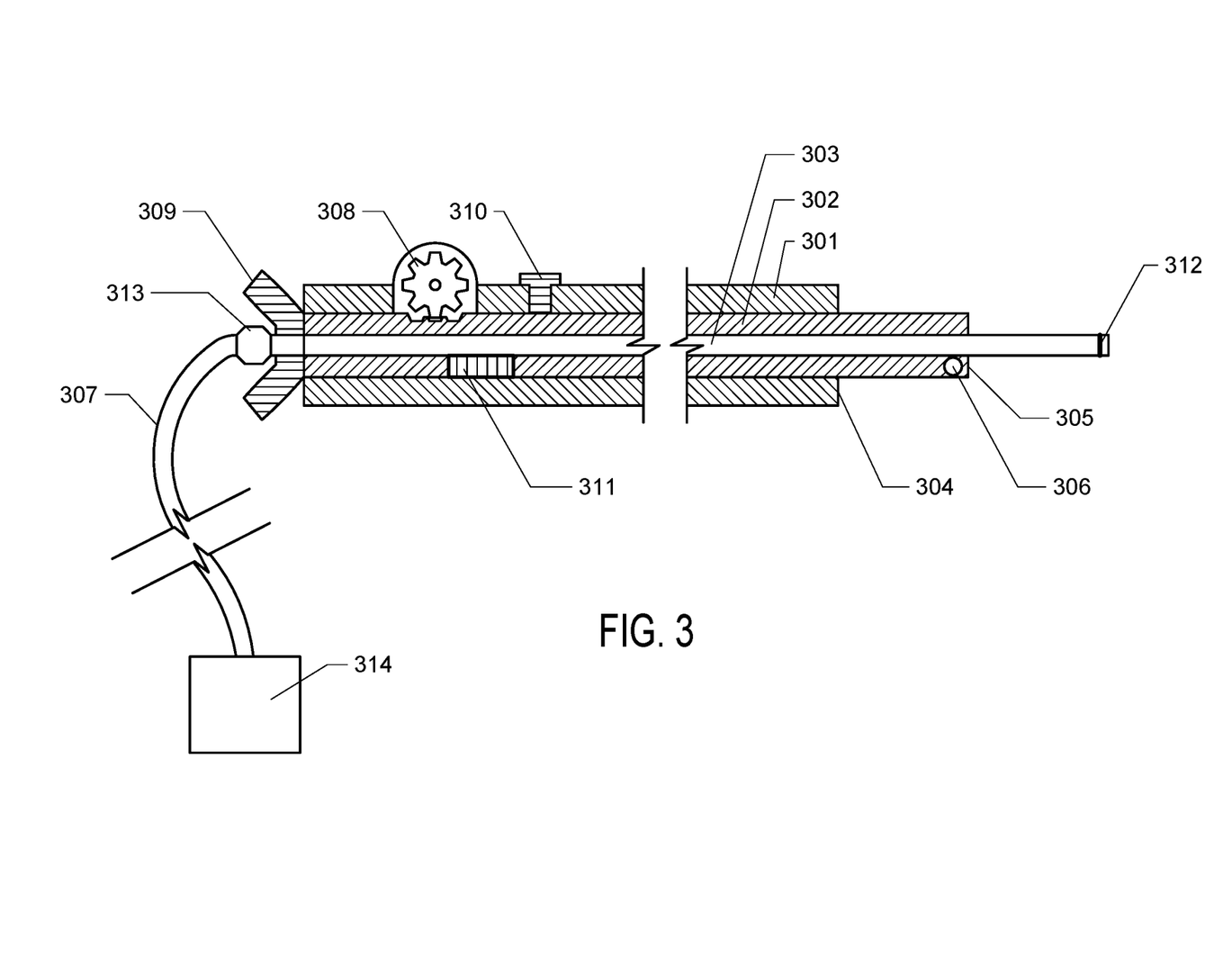
FIG. 3 depicts a cross sectional diagram of an exemplary stepped cannula of the invention. Note that the components are not depicted to scale.
Figure 4A:
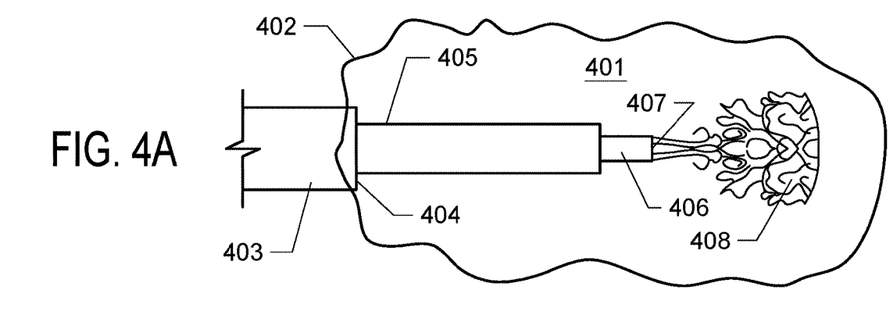
Figure 4B:
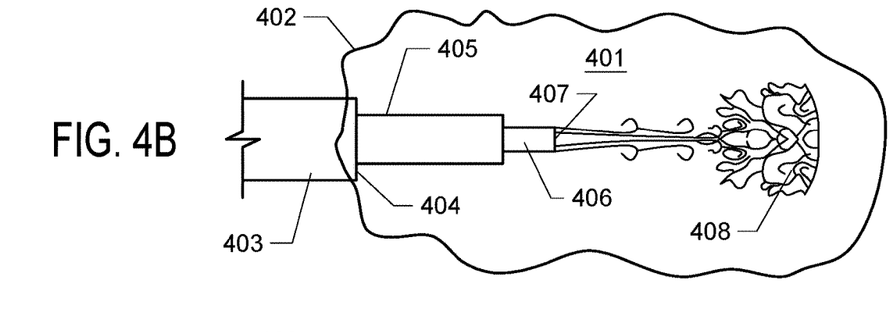
FIG. 4B depicts the cannula of FIG. 4A wherein the major step (404) remains in the same position and the adjustment tube (405) and dispensing tip (406) have been retracted to a second position. Delivered solution (408) permeates a portion of the target structure.
Figure 4C:
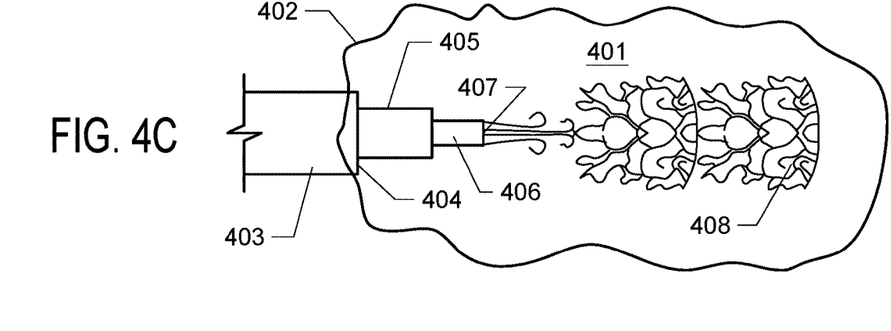
FIG. 4C depicts the cannula with the major step (404) remaining in the previous position and the adjustment tube (405) and dispensing tip (406) retracted to a third position, such that the delivered solution (408) has been delivered to a large portion of the target structure along the axis of movement of the dispensing tip.
Figure 5:
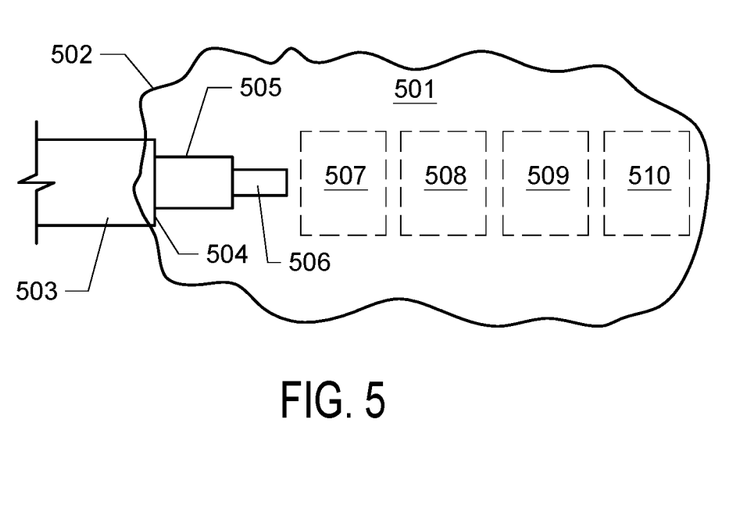
FIG. 5 depicts a target structure (501) and a cannula of the invention wherein the body tube (503) is positioned such that the major step (504) is located at the boundary or opening (502) of the target structure and the dispensing tip (506) is retracted. The dispensing tip assembly (505 and 506) may be extended and can deliver solution at various regions (507, 508, 509, and 510) along the long axis of the target structure.

An exemplary embodiment of the invention is depicted in the cross sectional diagram of FIG. 3 (it is noted that the components are not to scale in the diagram of FIG. 3). In this implementation of the invention, the cannula comprises three concentric tubes. The outermost tube is the body tube (301). Within the body tube is the adjustment tube (302). The inner diameter of the body tube and outer diameter of the adjustment tube are sized such that the adjustment tube can move within the body tube along the long axis of the body tube, i.e. the adjustment tube may telescope from or into the body tube. The innermost tube is the dispensing tube (303). The dispensing tube is fused, adhered, or otherwise fixed within the adjustment tube such that these two tubes move together within the body tube. In this embodiment, the adjustable tip of the invention comprises the intermediate tube and a dispensing tip. The dispensing tube comprises a lumen. At the proximal end of the lumen, the dispensing tube comprises a fitting (313) in connection with tubing (307) which is connected to a delivery solution supply (314), for example a reservoir and controllable pump. When the pump or other delivery supply is engaged, delivery solution flows through the dispensing tube and exits into the patient from the distal opening of the dispensing tube.

As depicted in the cross sectional diagram of FIG. 3, a section of the adjustment tube (302) protrudes from the distal end of the body tube. A section of the dispensing tube (301) further extends beyond the distal end of the adjustment tube. It is noted that in this configuration, a minor step (305) is formed at the distal end of the adjustment tube. The minor step creates backflow and aids in the dispersion of the delivered solution. The major step (304) creates a backstop which prevents backflow of infused agents along the cannula track and also aids in the dispersion of the delivered solution.

The proximal end of the cannula of the invention comprises an adjustment mechanism which enables an operator to shorten or lengthen the tip length. As depicted in FIG. 3, the adjustment mechanism may comprises a section of the adjustment tube which protrudes from the proximal end of the body tube and also comprises a handle or grip (309). This handle or grip of the adjustment tube can be gripped manually by the operator, which allows the operator to slide the adjustment tube in the proximal or distal direction, changing the length of the adjustable tip. The adjustment mechanism may also comprise a gear mechanism (308) which can engage teeth, indentations or projections on the outer surface of the adjustment tube, wherein turning of the gear can be used to extend or retract the adjustment tube, such that the tip length is changed.

The exemplary cannula of FIG. 3 also comprises a locking mechanism to fix tip length at a desired setting, the locking mechanism comprising a locking screw (310) which can be loosened during adjustment of tip length and then tightened to secure the adjustment tube in place at the desired position.

The exemplary cannula of FIG. 3 also comprises an indicator mechanism (311) which aids the user in precisely adjusting tip length, the indicator mechanism comprising a slot or opening in the body tube which allows graduated markings on the adjustment tube outer surface to be observed.

The exemplary cannula of FIG. 3 also comprises radio-opaque markings, which are visible to the operator via the selected radiological imaging modality used to place the cannula. One radio-opaque markings (306) is present near the major step. One radio-opaque marking (312) is also present at the distal end of the dispensing tip.

Cannula Composition and Sizing. The cannulas of the invention may be made of any suitable material known in the art for in vivo use. For example, stainless steel, titanium, or ceramics, for example zirconia, or other biocompatible materials may be used for the body tube, adjustment tube, and dispensing tube. The dispensing tube is preferably made of, or the inner lumen of the dispensing tube is preferably coated with, materials that are inert to and which do not substantially bind the delivered agents. For example, the dispensing tube may comprise fused silica tubing or polymer-coated stainless steel. Exemplary polymers include polyamide or polypropylene. Preferred materials for the cannula are those which do not have a "bending memory," and are able to return to a straight orientation if bent, preventing damage to surrounding tissues during cannula withdrawal.

The dimensions of the cannula components may be any as known in the art for effective convection-enhanced delivery of agents to the central nervous system. The exact specifications of the cannula will depend on the type of animal being treated and the depth of the organ or region of the central nervous system wherein the target resides. Typically, the "tubes" utilized in the components of the cannula are cylindrical, however square or other shapes may be used as well. For example, for delivery to the human brain, e.g. to the putamen, an exemplary cannula may comprise a body tube having an outer diameter of 4-6 mm and a length of 5-25 cm; an adjustment tube having an outer diameter of 2-4 mm, a dispensing tube having an outer diameter of 0.5-2 mm. The adjustable tip may be configured such that tip length ranges from of 0.1 to 4 cm long. For example, an exemplary adjustable tip for human intercranial delivery may be adjustable to tip lengths between 2 and 20 mm, with the distance between the dispensing portal and a minor step being 3-8 mm. In another example, an exemplary adjustable tip for non-human primate intercranial delivery may be adjustable to a length length between 2 and 18 mm, with the distance between the dispensing portal and a minor step being 1-6 mm. An exemplary inner diameter of the lumen of the dispensing tube of the cannulas of the invention may be, for example, in the range of 0.25-1.5 mm. For effective resistance to backflow, the major step will typically be in the range of 0.1 to 2 mm in width The cannulas of the invention may be configured in a variety of ways. The exemplary cannulas described herein have been described with respect to a single telescoping element, however it will be understood that two or more concentric telescoping elements may be used to change tip length. The exemplary cannulas depicted herein are typically substantially straight and rigid, however, the invention encompasses curved or flexible cannulas as well. The cannulas of the invention have been described and depicted herein as comprising cylindrical elements, however it will be understood that similar oblong elements may be used comprising squares, hexagons, octagons, and other shapes, for example with rounded edges.

Methods of Use. The invention further encompasses methods of using the cannulas described herein. In one embodiment, the invention comprises a general process as follows, it being understood that basic variation of the steps and the order of the steps are within the scope of the invention. In a first step, the cannula is inserted into the animal, e.g. into the skull if the brain is being treated. The insertion site may be selected in order to minimize side effects to the patient, as known in the art, for example such that the path length of the cannula to the target region is minimized, or such that less sensitive regions of the brain are disturbed by the cannula. Exemplary insertion sites include frontal, parietal and occipital approaches to target structures. The insertion and placement of the cannula is guided by radiographic imaging (e.g. MRI, CT, X-Ray, etc.), optionally with the assistance of contrast agents that have been injected or administered to the animal or the target region of the animal to aid in the visualization of structures within the patient.

The cannula tip and/or major step may also be viewed by radiographic imaging, for example if the cannula materials are radio-opaque or if the cannula tip and/or major step have been adorned with radio-opaque markings. Viewing the target region and cannula tip via a radiographic imaging modality such as MRI, the operator positions the cannula such that the major step, at the distal end of the body tube, is located at or just within the boundary or opening of the target structure.

Once the cannula is deployed with the major step in optimal position, the operator may adjust the tip length to effect optimal placement of the tip's distal opening, for example extending the tip if the cannula has been deployed with the tip in a retracted position. In one embodiment, the cannula is initially deployed with the adjustable tip retracted to its shortest length. In one embodiment, the cannula is initially deployed with the adjustable tip completely retracted within the body tube. Once the tip is positioned optimally, e.g. in the center of the target region, solution is flowed by engaging the delivery solution supply, at flow rates sufficient to effect CED.

In one embodiment, while the major step is maintained in a fixed position, delivery solution is dispensed at two or more points within the target structure changing tip length, allowing the operator to effect a varied delivery profile for the agent from a single cannula placement. The adjustable tip may be extended or withdrawn from the cannula body such that therapeutic solution is delivered at multiple points along the axis of movement of the tip. The telescoping adjustable tip can be held stationary at each selected delivery point for a time interval while solution is dispensed. Alternatively, the delivery solution may be dispensed continuously while the telescoping adjustable tip is slowly moved inward towards or outward from the major step, to create a delivery profile along the axis of movement.

The adjustable stepped cannulas of the invention are especially useful in the administration of agents to elongate structures, such as the putamen or caudate. The cannula approach and trajectory can be planned to align with the long axis of the target structure. Once inserted, for example with the major step at the boundary or opening of the target structure, solution can be it can be delivered in two or more locations along the length of the structure during a treatment by retracting or extending the adjustable tip, creating an elongated delivery profile along the long axis of the target structure. This advantageously allows a single cannula placement to effectively deliver agent to the entire structure, obviating the need for additional cannula insertions. For example, two, three, four, or more positions within the target structure may be treated by moving the tip to different positions and dispensing solution at each such position.

The methods of the invention encompass the delivery of a solution to a target structure, wherein such solution is delivered by the use of a stepped cannula having an adjustable tip. The solution comprises one or more agents, the agents being dissolved, suspended, or otherwise present in a carrier liquid, for example a biocompatible liquid, e.g. a buffer or saline solution. The one or more agents may comprise a therapeutic composition, for example a drug (e.g. a chemotherapeutic drug), a protein (e.g. a growth factor or antibody), or a nucleic acid construct (e.g. a gene therapy vector).

The one or more agents may also comprise an imaging composition, e.g. a dye or contrast agent, for example a gadolinium contrast agent for MRI imaging. The imaging agent allows the operator to visualize the dispensed solution and to assess the degree of coverage of the dispensed solution in the target region.

It will be understood that the devices and methods of the invention may be applied to any internal tissue of an animal, especially the structures of the central nervous system, including the brain. For example, the delivery solution may be administered in the putamen, the caudate nucleus, dorsal raphe, locus ceruleus, brain stem, thalamus, hippocampus or any other known structure of the brain. It will be understood that while reference is made herein to treating a "patient," implying a human subject in need of medical attention, the devices and methods of the invention may be applied to any animal species, including humans, non-human primates, rodents, canines, felines, bovines, and other species. The devices and methods of the invention may be applied in medical, veterinary, or research contexts.

EXAMPLE 1

An adjustable stepped cannula was made having a fused silica dispensing tube and a ceramic adjustment tube, the two being fused and movable within the body tube of the cannula by action of a gear mechanism. The minor step was located 3 mm from the tip. The distance between the tip and the major step was adjustable, for example being extendable to 10, 15, or 18 mm long in various prototypes. The adjustable stepped cannula of the invention was tested in non-human primates. The caudate nucleus was targeted from either the occipital and parietal approaches, allowing cannula insertion along the long axis of the structure. MR imaging allowed visualization of target structures and placement of the cannula. A solution comprising gadolinium contrast agent and an adeno-associated viral vector carrying an Aromatic L-amino acid decarboxylase gene (AAV2-AADC) was delivered. The initial infusion was done with tip fully retracted. The infusion continued as the tip and minor step were gradually extended and deployed into the structure. Visualization of gadolinium showed that the infused bolus tracked the movement of the cannula tip and closely mimicked the shape of the target anatomical structure. Subsequent immunostaining of AADC showed that the gene vector was successfully delivered within the boundaries of the infusion. The same approach was also successfully applied for infusion in the hippocampus, putamen, and thalamus in the non-human primate subjects.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of performing convection-enhanced delivery of a solution to a target structure within the body of an animal, comprising the steps of:
   introducing an adjustable stepped cannula into the body of the animal, such introduction being guided by external radiographic imaging of the distal end of the cannula, and wherein the adjustable stepped cannula is a device comprising:
      an elongated body comprising a proximal and a distal end, wherein the cannula is configured such that when in use, the proximal end of the cannula body is outside the animal and the distal end is inserted into the animal;
      wherein the cannula body contains a telescoping element comprising a proximal end and a distal end and wherein the device is configured such that a portion of the distal end of the telescoping element can be extended to protrude from the distal end of the body of the cannula;
      wherein the width of the telescoping element is less than that of the body, such that a step is formed at the distal end of the body around the distally protruding portion of the telescoping element, wherein the step comprises a face or surface perpendicular to the long axis of the cannula and capable of blocking backflow of infused solution;
      wherein the telescoping element comprises an internal lumen, wherein the proximal end of the lumen is configured for connection with a supply of the solution and the distal end of the telescoping element comprises an opening from which the solution may be flowed from the lumen into the animal;
      wherein the proximal end of the adjustable stepped cannula that is outside the body of the animal comprises an adjustment mechanism, by which the telescoping element may be controllably moved distally and proximally within the body of the cannula such that the cannula comprises an adjustable tip, the adjustable tip comprising the portion of the telescoping element which protrudes from the distal end of the body, wherein the length of the adjustable tip is the distance between the step and the distal end of the telescoping element, and wherein the length of the adjustable tip may be adjusted by a user by the adjustment mechanism while the cannula is deployed in the animal;
   positioning the adjustable stepped cannula such that the step is located at or near the boundary or opening of the target structure, such positioning being enabled by external radiographic imaging of the step;
   by the adjustment mechanism, changing the length of the adjustable tip such that the distal opening thereof is positioned in a desired placement with respect to the target structure, such positioning being enabled by external radiographic imaging of the distal end of the adjustable tip; and
   engaging the supply of solution such that solution flows through the lumen of the telescoping element and exits the distal opening of the adjustable tip into the target structure.

2. The method of claim 1, wherein the adjustment of the adjustable tip length is made while maintaining the position of the step in the animal.

3. The method of claim 1, wherein the target structure is in the brain.

4. The method of claim 3, wherein the target structure is selected from the group consisting of the putamen, the caudate nucleus, dorsal raphe, locus ceruleus, brain stem, thalamus, and hippocampus.

5. The method of claim 1, wherein the animal is a human patient.

6. The method of claim 1, wherein the solution comprises a therapeutic agent.

7. The method of claim 6, wherein the therapeutic agent comprises a drug, a protein, or a nucleic acid construct.

8. The method of claim 1, wherein the solution comprises an imaging agent.

9. The method of claim 8, wherein the imaging agent is gadolinium.

10. The method of claim 1, wherein the adjustable stepped cannula further comprises a locking mechanism, wherein the locking mechanism, when engaged, holds the telescoping element in a fixed position with the body of the cannula.

11. The method of claim 1, wherein the adjustable stepped cannula further includes a minor step, the minor step being an abrupt reduction in the width of the telescoping element, the distal end of the telescoping element being narrower than the proximal end.

12. The method of claim 1, wherein the adjustable stepped cannula further includes a visual indicator disposed at or near the proximal end of the cannula which allows the operator to determine the length of the adjustable tip.

13. The method of claim 1, wherein the telescoping element comprises ceramic and the lumen of the telescoping element comprises fused silica or polymer.

14. The method of claim 1, wherein the adjustable tip has a length that can be adjusted between 1 and 40 mm.

15. The method of claim 1, wherein the step formed at the distal end of the body has a width of 0.1 to 2 mm.

* * * * *

UNITED STATES PATENT AND TRADEMARK OFFICE
CERTIFICATE OF CORRECTION

| | | |
|---|---|---|
| PATENT NO. | : 11,583,311 B2 | Page 1 of 1 |
| APPLICATION NO. | : 16/921604 | |
| DATED | : February 21, 2023 | |
| INVENTOR(S) | : Krystof S. Bankiewicz | |

It is certified that error appears in the above-identified patent and that said Letters Patent is hereby corrected as shown below:

In the Specification

In Column 5, Line 45, delete "indicatorechanism" and insert -- indicator mechanism --.

In Column 7, Line 49, delete "width" and insert -- width. --.

In Column 9, Line 21, delete "ceruleus," and insert -- coeruleus, --.

In the Claims

In Column 11, Line 5, in Claim 4, delete "ceruleus," and insert -- coeruleus, --.

Signed and Sealed this
Eleventh Day of April, 2023

Katherine Kelly Vidal
*Director of the United States Patent and Trademark Office*